United States Patent [19]

Chet et al.

[11] Patent Number: 4,713,342

[45] Date of Patent: Dec. 15, 1987

[54] NOVEL ISOLATE OF TRICHODERMA, FUNGICIDAL COMPOSITIONS CONTAINING SAID ISOLATE AND USE THEREOF

[75] Inventors: Ilan Chet; Alex Sivan, both of Ness Ziona; Yigal Elad, Kibbutz Netzer Sireni, all of Israel

[73] Assignee: Yissum Research Development Co. of the Hebrew University of Jerusalem, Jerusalem, Israel

[21] Appl. No.: 588,950

[22] Filed: Mar. 13, 1984

[30] Foreign Application Priority Data

Mar. 15, 1983 [IL] Israel ......................................... 68129

[51] Int. Cl.⁴ ...................... C12N 1/14; A61K 35/70; A01N 63/04
[52] U.S. Cl. ..................................... 435/254; 424/93; 71/3
[58] Field of Search .................. 435/258, 254; 424/93; 71/3

[56] References Cited

U.S. PATENT DOCUMENTS 4,439,455  3/1984  Villettag ............................. 435/945
4,489,161  12/1984  Papavizas ........................... 435/911

OTHER PUBLICATIONS

Biosis Abstract, Kraft et al., Plant Dis, vol. 67(11), 1983, 1234–1237.
Biosis Abstract, Papavizas et al., Phytopathology; 71(2), 1981 pp. 247–248.
Chemical Abstract, vol. 84, Abstract No. 100690c, 1975.

*Primary Examiner*—Blondel Hazel
*Attorney, Agent, or Firm*—John P. White

[57] ABSTRACT

A biological control agent comprising the mycoparasite *Trichoderma harzianum* T-315 (ATCC No. 20671), which is characterized by fungicidal activity against fungi of the genera Pythium, Phizoctonia, Sclerotium and Fusarium. This strain is useful for controlling damping-off, root-rot, crown-rot and neck-rot in seedling crops. This strain is also resistant to chemical pesticides and soil-sterilants and useful for integrated biological and chemical control of soil-borne pathogens.

15 Claims, 1 Drawing Figure

NOVEL ISOLATE OF TRICHODERMA, FUNGICIDAL COMPOSITIONS CONTAINING SAID ISOLATE AND USE THEREOF

FIELD OF THE INVENTION

The present invention relates to antifungal compositions, particularly to biological control compositions containing Trichoderma harzianum and to methods of protecting plants from soil-borne pathogenic fungi with such compositions.

BACKGROUND OF THE INVENTION

Soil-borne pathogenic fungi cause damping off, root-rot, crown-rot and neck-rot in a wide variety of seedling crops. Among these pathogenic fungi are fungi of the genera Rhizoctonia, Pythium, Sclerotium, Phytophotora and Fusarium. These fungi are capable of attacking and causing extensive damage to many common and commercially important crops, such as beans, tomatoes, cotton, peanuts, potatoes, lettuce, ornamental flowers and others.

Chemical fungicides have been widely used to control these soil-borne pathogens. The use of such chemicals is expensive and may result in ecological damage and in the increased incidence of occupational diseases. A promising alternative to such chemical control is the biological control of soil plant pathogens by naturally-occurring microorganisms. These biological control agents may be used alone or in conjunction with lesser amounts of chemical fungicides.

The use of antagonistic microorganisms in controlling plant pathogenic fungi has been the subject of extensive research. A large part of this research has been concerned with myco parasitism, the parasitism by one fungus of another. One of the most frequently studied mycoparasites in relation to biological control is the genus Trichoderma. (Y. Elad et al., 1982, Can. J. Microbiol. 28: 719–725, I. Chet and R. Baker, 1981, Phytopathology 71: 286–290; M. N. Schroth and J. G. Hancock, 1981, Ann. Rev. Microbiology 35: 459–463; Y. Elad, et al., 1981, Plant Disease 65:675–677; Y. Elad, et al., 1980, Phytopathology 70: 119–121; I. Chet et al., 1979, in B. Scippers and W. Gams. eds, "Soil Borne Plant Pathogens", Academic Press, NY, NY; Y. Hadar et al., 1979, Phytopathology 69:64–68; C. Dennis and J. Webster, 1971, Trans. Br. mycol. Soc. 57(3), 363–369).

Species or strains of Trichoderma may be differentially antagonistic to different species of fungi. (H. D. Wells et al., 1972, Phytopathology 62:442–447). Such differences in antagonism have been found both within and between species of Trichoderma (D. K. Bell et al., 1982, Phytopathology 72:379–382).

In addition to such differences in antagonism, it has been determined that the environment in which the interaction occurs also affects the degree of biological control. Antagonism in culture is often not reproducible in the complex environment present in the soil under greenhouse or field conditions. (M. N. Schroth and J. G. Hancock, 1981, Ann. Rev. Microbiol. 35:453–76). As a result, tests made under non-soil culture conditions are not truly indicative of the potential for use of the Trichoderma isolate as a biological control agent.

Due to the significant differences in antogonism of Trichoderma isolates to various pathogens under different environmental conditions, researchers have concentrated their efforts on searching for Trichoderma antagonists against specific disease causing plant pathogenic fungi. The likelihood of finding a specific biological antagonist with a wide range of antagonism under field conditions to several species of plant pathogens was considered remote. (D. K. Bell et al., 1982, Phytopathology 72:379–382).

SUMMARY OF THE INVENTION

A novel mycoparasite of the species Trichoderma harzianum has been discovered which is fungicidally active against pathogenic fungi of the genera Pythium, Rhizoctonia, Sclerotium and Fusarium. This mycoparasite is useful in controlling plant diseases such as damping-off, crown-rot, root-rot and neck-rot, which are caused by soil-borne pathogenic fungi. The preferred strain of the invention is Trichoderma harzianum Rifai T-315 (ATCC No. 20671) and it has been cultured in a biologically pure culture.

T. harzianum T-315 (ATCC No. 20671) possesses resistance to chemical pesticides which would kill or retard the growth of other fungi. Such pesticides include PCNB, previcur, captan and Dexon ®, but are not limited to this group. T. harzianum T-315, (ATCC No. 20671) also possesses resistance to soil sterilants, such as methyl bromide. Resistance to such chemical antagonists enables the invention to be used in integrated chemical and biological control of plant pathogens.

This novel strain of Trichoderma harzianum may be mixed with a suitable agriculturally acceptable carrier to produce a fungically active, biocontrol composition useful in controlling diseases caused by soil-borne plant pathogenic fungi. This biocontrol composition may also contain a food base for the mycoparasite or the carrier itself may also serve as the food base.

The invention also concerns methods of using this biocontrol composition as a fungicide. Effective amounts of the biocontrol composition are applied to or incorporated in soil in which plant seedlings are grown. Potted seedlings may also be protected from attack by soil-borne pathogenic fungi by potting them in soil containing an effective amount of the biocontrol composition.

In a specific embodiment of the invention, a chemical pesticide is included in the biocontrol composition. Alternatively, the chemical pesticide is applied to or incorporated into soil containing the biocontrol composition. The soil in another embodiment of the invention is sterilized, e.g., with methyl bromide, before the application of the biocontrol composition.

In other embodiments of the invention the biocontrol composition also contains a suitable agriculturally acceptable adhesive. This biocontrol composition is used to coat fruits and plant seeds in order to protect them from diseases caused by soil-borne pathogenic fungi.

DETAILED DESCRIPTION OF THE INVENTION

Figure 1:
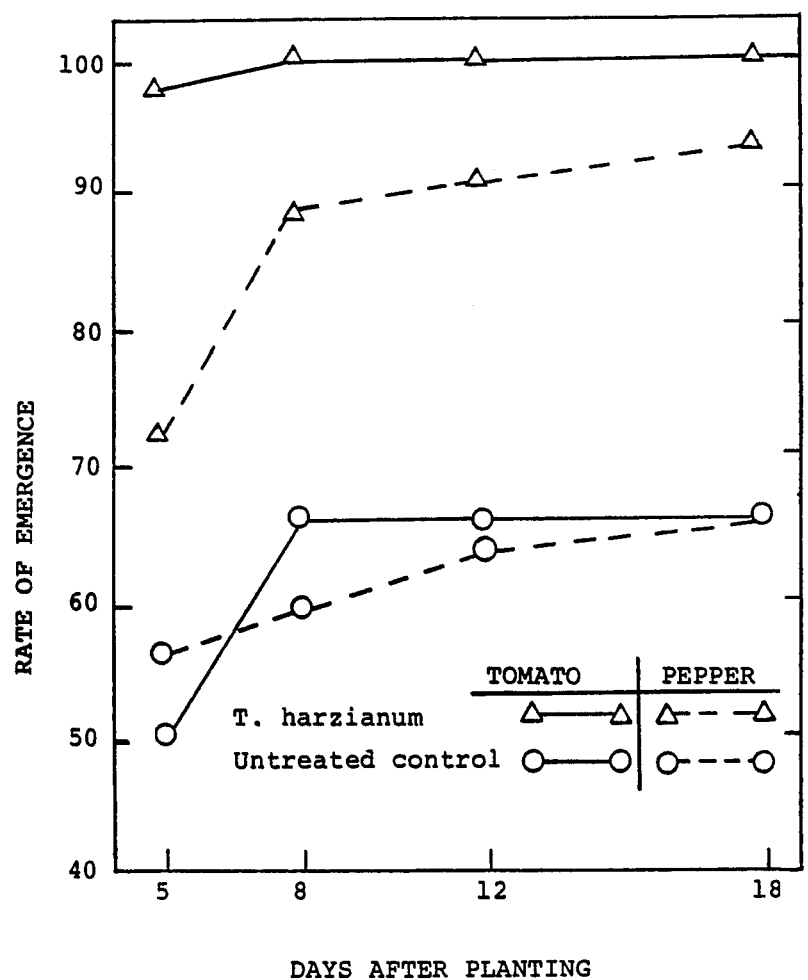
FIG. 1. A comparison of the rate of emergence of tomato and pepper seedlings grown in peat naturally infested with P. aphanidermatum with the rate of emergence of tomato and pepper seedlings grown in peat naturally infested with P. aphanidermatum containing 20% by volume of T. harzianum T-315 (ATCC 20671) incorporated therein.

A novel mycoparasite of the species *Trichoderma harzainum* has been discovered which is fungicidally active against pathogenic fungi of the species *Pythium aphanidermatum, Rhizoctonia solani, Sclerotium rolfsii* and *Fusarium* spp. The preferred strain of this novel mycoparasite was isolated from a soil naturally infested witth *Pythium* species and identified according to the criteria of Rifai, (Rifai M, 1969, Mycol. Pap 116). It has been cultured in a biologically pure form. The preferred strain *Trichoderma harzianum* Rifai T-315, is deposited with the American Type Culture Collection, Rockville, Md. 20852, pursuant to the provisions of the Budapest Treaty on the International Recognition of the Deposit of Microorganisms for the Purposes of Patent Procedure under accession number ATCC 20671.

*T. harzianum* T-315, (ATCC No. 20671), and mutants derived therefrom may be used to control plant diseases such as damping-off, root-rot, crown-rot and neck-rot, which are caused by the fungi, *R. solani, P. aphanidermatum* (Edson) Fitz, *S. rolfsii* and *Fusarium* spp.

In addition to fungicidal activity and long-term survivability, *T. harzianum* T-315, (ATCC No. 20671) possesses resistance to several chemical pesticides which would kill or retard the growth of other fungi. Such pesticides include, but are not limited to, the fungicides: Dexon ® (P-dimethylaminobenzendiazo sodium sulfonate) and previcur (S-ethyl-N-[3-dimethylaminopropyl] thiocarbamate), which are commonly used to control fungi of the genus *Pythium*, Terraclor ® (PCNB-Pentachloronitrobenzene) which is commonly used to control fungi of the genus *Rhizoctonia*, and captan (N-[trichloromethyl thio]-4-cyclohexene-1,2-dicarboximide). *T. harzianum* T-315, (ATCC No. 20671) also possesses resistance to chemical soil sterilants, such as methyl bromide which is commonly used to control soil-borne pests such as *Fusarium* spp. and nematodes.

This high degree of resistance to chemical antagonists enables *T. harzianum* T-315, (ATCC No. 20671) to be used in integrated biological and chemical control of pathogenic fungi. In a specific embodiment of this invention *T. harzianum* T-315, (ATCC No. 20671), is applied to the soil together with sub-lethal doses of previcur or terraclor in order to control *R. solani* and *P. aphanidermatum*. This integrated control method prevents the common and undesirable phenomenon of enhanced *R. solani* disease incidence upon exclusively controlling *P. aphanidermatum* with previcur, or alternatively the enhanced *P. aphanidermatum* disease incidence upon exclusively controlling *R. solani* with terraclor. This phenomenon which results from the mutual antagonism of *R. solani* and *P. aphanidermatum* is controlled by *T. harzianum* T-315 (ATCC No. 20671) which possesses fungicidal activity against both of these fungi in the same environment.

The novel *T. harzianum* strain of this invention is capable of simultaneously controlling the fungi *S. rolfsii* and *Fusarium* spp. in addition to *R. solani* and *P. aphanidermatum*. In other embodiments of this invention *T. harzianum* T-315 (ATCC No. 20671), can be used as a bio-control agent in combination with sub-lethal doses of other chemical antagonists to which it is resistant to control plant diseases caused by a wide range of plant pathogens.

One other embodiment of the invention, is the use of *T. harzianum* T-315, (ATCC No. 20671) in conjunction with a soilsterilant such as methyl bromide. The soil is first fumigated with the soil-sterilant, and then the biocontrol agent is applied. Fumigation prior to the application of the biocontrol agent, allows the *T. harzianum* T-315, (ATCC No. 20671) to establish itself in the soil and thus control of plant pathogens and crop yields are enhanced.

In addition to its wide range of antagonism and resistance to chemical pesticides, *T. harzianum* T-315 (ATCC No. 20671) is capable of long term survivability and of controlling diseases caused by soil-borne pathogens throughout a 20° C. to 35° C. temperature range. These additional characteristics make the present invention a versatile biocontrol agent suitable for application in semi-arid as well as temperate agricultural zones. There are a variety of possible methods of applying the present invention. One method is the application of *T. harzianum* T-315, (ATCC No. 20671), conidia or chlamydospores or mixtures of the two, directly to the soil. The conidia of *Trichoderma* spp. are the active antagonistic structures of the fungus, whereas the chlamydospores are the fungal long-term survivable resting structures. Direct application of the mycoparasite, however, seems to be less effective than the application of a biocontrol composition which contains *T. harzianum* T-315 (ATCC No. 20671) and an agriculturally acceptable carrier. The biocontrol compositions may be applied directly to the soil in which the plant is growing, or the seedling itself may be potted in soil containing an effective amount of the biocontrol composition.

These biocontrol compositions may be in a solid or a liquid form and may include other adjuvants such as emulsifiers, suspending agents, sticking agents etc. The solid compositions may be in the form of dusts, granules, or wettable powders, whereas the liquid compositions may be in the form of aqueous or non-aqueous media, in solution, suspension, dispersion or concentrate form.

The quantity of spores, conidia or chlamydospores, of the mycoparasite in the composition should be at least $10^5$ and preferably above $10^7$ spores per gram of composition. Propagation of these spores depends upon growth conditions within the composition or in the soil to which it is applied. Such factors as the storage time of the composition may have an effect on the growth conditions of the composition and therefore it is preferred to prepare compositions which contain a suitable food base.

In certain embodiments of the invention the carrier may constitute wholly or in part a food base for the mycoparasite. Such food bases are known to those of ordinary skill in the art and may constitute agricultural waste products. Some suitable food bases are wheat bran, peat, milled corn cobs, ground wheat straw, and ground cotton straw. A preferred food base is a 1:1 mixture of wheat bran and peat. These food bases are usually sterilized and moistened. The food base and carrier provide the mycoparasite with sufficient nutrients and a favorable microenvironment facilitating its establishment and long term survival in the soil.

In other embodiments of the invention, the biocontrol composition may also contain another pesticide. This pesticide may be a chemical pesticide to which *T. harzianum* T-315, ATCC No. 20671), is resistant, such as Dexon ®, Terraclor ®, previcur or captan. The pesticide may also be another biocontrol agent such as a mycoparasite of a different species of Trichoderma.

For application in the fields, ten to five hundred grams and preferably fifty to one hundred grams (dry weight), of the biocontrol composition are applied to each square meter of soil. The biocontrol composition is spread in the seeding rows and then incorporated into the soil. In the greenhouse, the biocontrol composition is applied at the rate of one to ten grams (dry weight) per kilogram of soil and preferably at the rate of five grams per kilogram of soil.

In a specific embodiment of the invention, the biocontrol composition also contains a suitable agriculturally acceptable adhesive, e.g., Pelgel ® (Nitragin, Wisc. USA). This biocontrol composition containing the adhesive can be applied to seeds as a seed coating before planting, and also to fruits in order to protect them from diseases caused by soil-borne pathogens.

The range of host plants that are subject to attack by the soil-borne pathogens P. aphanidermatum, S. rolfsii, R. solani and Fusarium spp. is very broad. This invention is effective in controlling diseases caused by these soil-borne pathogens over this wide range, and is effective in protecting such plants as beans, peas, tomatoes, cucumbers, peppers, cotton, peanuts, potatoes, lettuce, strawberries, tobacco, forest trees, ornamentals, carnations, irises, gypsophilea, chick peas, carrots, eggplants and other seedlings.

EXAMPLES

EXAMPLE 1

A Trichoderma species was isolated from a soil naturally infested with Pythium species as follows:

1 g sample of the soil was suspended in 100 g water and shaken at 400 rpm. Portions of the liquid were diluted with a 0.01% bacto-agar solution three times and 0.1 ml of the serial dilutions were grown on selective media agar plates (Elad et al., Phytoparasitica, 1981, Vol. 9, pages 59–67). The resultant pure strain was named T-315. This isolate was grown for fourteen days at 30° C. on a 1:1 wheat bran: peat, tap water mixture (40% water) which was autoclaved for one hour at 121° C. on two successive days.

EXAMPLE 2

T. harzianum T-315 (ATCC No. 20671) was grown on agricultural wastes as food bases and was incubated at the temperature of 30° C. for a week and then tested for growth rate. Survivability was tested after incubation of one year at room temperature. Growth vigor and survivability are expressed as number of viable propagules/g. preparation (dry weight) and are shown in Table 1.

TABLE I

Growth Vigor and Survivability of T. harzianum T-315 (ATCC No. 20671) Grown on Agricultural Wastes

| | No. of viable Propagules/g composition (dry weight)[1] | | |
|---|---|---|---|
| | | After 1 yr storage at room temperature | |
| Food Base | After 7 days at 30° C. | No Chl.[2] | Chl.[2] Supplemented |
| Wheat Bran: peat (1:1) (v/v) | $5.1 \times 10^9$ | $4.4 \times 10^8$ | $9.5 \times 10^8$ |
| Wheat Bran | $8.0 \times 10^8$ | $1.2 \times 10^7$ | $2.4 \times 10^7$ |
| peat | $8.0 \times 10^8$ | $7.3 \times 10^6$ | $8.5 \times 10^6$ |
| Ground Peat | $4.5 \times 10^8$ | $2.3 \times 10^7$ | $2.1 \times 10^7$ |
| Ground Wheat Straw | $4.9 \times 10^8$ | $2.5 \times 10^5$ | $2.2 \times 10^7$ |
| Ground Cotton Straw | $4.0 \times 10^7$ | $2.1 \times 10^5$ | $2.5 \times 10^5$ |

[1]Initial no of T. harzianum propagules - $4 \times 10^2$ conidia/g substrate
[2]Chl. - Chloramphenicol, 250 mg.

Wheat bran, peat or a mixture of the two appear to be the food bases best utilized by the Trichoderma. The other food bases shown are also quite acceptable.

EXAMPLE 3

T. harzianum T-315 (ATCC No. 20671) was incorporated into a composition comprising wheat-bran: peat (1:1) (v/v) (40% (w/w) moistened), hereinafter referred to as T. harzianum composition. The composition was applied to sandy-loam soils artificially infested with Pythium aphanidermatum and to peat naturally infested with P. aphanidermatum, at 5 g composition/kg soil in the greenhouse.

As shown in Table 2, the T. harzianum successfully reduced disease levels in a variety of crop seedlings.

TABLE 2

The Effect of T. harzianum T-315 (ATCC 20671) on the Control of Diseases Caused by P. aphanidermatum in Cucumbers, Tomatoes, Peas, Beans, Peppers and Gypsophila Cuttings.

| | Artificially Infested Soil | | Naturally Infested Peat | |
|---|---|---|---|---|
| Crops | Diseased Plants (%) (untreated control) | Diseased Plants (%) (treated soil) | Diseased Plants (%) (untreated control) | Diseased Plants (%) (treated peat) |
| Cucumbers | 91.2 | 27.8 | 85.9 | 48.5 |
| Tomatoes | 36.0 | 14.4 | 76.1 | 3.5 |
| Peas | 77.2 | 8.8 | — | — |
| Beans | 80.6 | 10.2 | — | — |
| Peppers | — | — | 41.7 | 7.3 |
| Gypsophila Cuttings | — | — | 97.9 | 33.3 |

EXAMPLE 4

T. harzianum T-315 (ATCC 20671), composition of Example 3 was incorporated into sandy-loam soils which were artificially infested with R. solani and S. rolfsii, at a rate of 5 g per kg soil. The experiment was carried out in the greenhouse with beans as the test plants.

As can be seen from Table 3, diseases caused by both of these pathogens were controlled by the Trichoderma, the reduction of S. rolfsii incidence being particularly marked.

TABLE 3

The Effect of T. harzianum T-315 (ATCC 20671) on the Control of R. solani and S. rolfsii Diseases in Beans.

| Treatment | Soil Infested with R. solani | | Soil Infested with S. rolfsii | |
|---|---|---|---|---|
| | Diseased Plants (%) | Disease Reduction (%) | Diseased Plants (%) | Disease Reduction (%) |
| Control | 33.9 A[1] | — | 49.1 A | — |
| T. harzianum T-315 (ATCC 20671) | 21.3 B | 37.5 | 12.0 B | 75.6 |

[1]Numbers followed by dissimilar letters, within columns, are significantly different (P = 0.05)

EXAMPLE 5

Sandy-loam soils (pH 7.2) were artificially infested with the pathogen Sclerotium rolfsii at the rate of 0.05 g sclerotia/kg soil. Beans (Phaseolus vulgaris L.) were used as test plants for the determination of the control efficiency of various preparations of T. harzianum T-315 (ATCC 20671) with the food-bases listed below. The experiment was carried out in the greenhouse.

As illustrated in Table 4, all the tested compositions significantly reduced the number of diseased plants. The wheat-bran:peat (1:1) composition was found to be particularly effective

TABLE 4

The Effect of Various T. harzianum T-315 (ATCC 20671) Compositions on the Control of S. rolfsii in Beans.

| Preparation[1] | Diseased Plants (%) | Disease Reduction (%) |
|---|---|---|
| Control | 63.3 A[2] | |
| Peat | 26.7 B | 57.8 |
| Ground Wheat Straw | 25.0 B | 60.5 |
| Ground Cotton Straw | 20.0 B | 68.4 |
| Wheat-Bran | 16.7 B | 73.6 |
| Wheat-Brand:Peat (1:1) (v/v) | 13.3 B | 79.9 |

[1]Each of the listed food-bases was inoculated with a conidial suspension of T. harzianum T-315 (ATCC 20671) incubated for 7–10 days in an illuminated chamber at the temperature of 30° C. The moisture level of the above compositions was 40% (w/w). The preparations were incorporated into the soils at the rate of 5 g/kg soil.
[2]Numbers followed by dissimilar letters, within columns, are significantly different (P = 0.05).

EXAMPLE 6

Peat, naturally infested with P. aphanidermatum, was seeded with tomato and pepper seeds. T. harzianum T-315 (ATCC 20671), was incorporated into the peat to comprise 20% by volume. The experiment was carried out in the greenhouse.

The rate of emergence of tomato and pepper seedlings was greatly improved by the T. harzianum, as illustrated in FIG. 1.

EXAMPLE 7

Cucumber and pea seeds were coated with T. harzianum T-315 (ATCC 20671), conidia, using Pelgel ® Nitragin, Wisc., USA) as an adhesive matrix. The coated seeds were seeded in sandy soils artificially infested with P. aphanidermatum. The effect of application of the T. harzianum as a seed coating on the Pythium disease incidence was compared with that of the T. harzianum soil treatment.

Both treatments successfully controlled the pathogenic fungus. No significant difference between the two was found as shown.

TABLE 5

The Effects of T. harzianum T-315 (ATCC 20671) Seed Coating and Soil Treatment on P. aphanidermatum Diseases in Peas and Cucumbers.

| Treatment | Diseased Plants (%) | |
|---|---|---|
| | Cucumber | Pea |
| Control | 27.8 A[1] | 37.8 A |
| T-315 Seed Coating | 6.7 B | 4.4 B |
| T-315 Soil Treatment | 8.6 B | 7.0 B |

[1]Numbers followed by dissimilar letters, within columns, are significantly different (P = 0.05)

EXAMPLE 8

Pea seeds coated with T. harzianum T-315 (ATCC 20671) conidia were seeded in soil naturally infested with P. aphanidermatum. The experiment was carried out in a growth chamber at the constant temperature of 22° C.

The seed coating treatment reduced the disease level by 44% in comparison with the untreated seeds, thus showing the biocontrol capability of T. harzianum T-315 (ATCC 20671), even under relatively low temperatures.

EXAMPLE 9

The effect of four commonly used fungicides on the growth rate of Trichoderma T-315 (ATCC 20671) was tested in culture. The following fungicides were tested:

Terraclor ®—Pentachloronitrobenzene (PCNB) (Olin Chemicals, U.S.A)

Previcur—S-ethyl N-(3-dimethylaminopropyl) thiocarbamate (Schering A.G., Germany)

Captan—N-(trichloromethyl thio)-4-cyclohexene-1,2-dicarboximide (Makteshim, Israel)

Dexon ®—P-dimethylaminobenzene diazo sodium sulfonate (Farbenfabrix Bayer A.G., Germany)

T-315 isolate exhibits very high resistance to Terraclor and Previcur, and considerable resistance to Dexon and Captan. The results are presented in Table 6.

TABLE 6

Inhibitory Effects of the Fungicides Terraclor, Previcur, Captan and Dexon on the Vegetative Growth of T. harzianum T-315 (ATCC 20671).

| Conc.[1] | Inhib.[2] | Conc.[1] | Inhib.[2] |
|---|---|---|---|
| Terraclor | | Previcur | |
| 50 | 29.7D[3] | 1,000 | 6.3B |
| 100 | 53.1C | 1,500 | 8.3B |
| 1,000 | 55.9C | 2,000 | 10.0AB |
| 3,000 | 69.5B | 3,000 | 14.5A |
| 10,000 | 78.5A | | |
| Captan | | Dexon | |
| 10 | 17.4C | 10 | 11.5B |
| 20 | 21.4C | 100 | 15.0B |
| 100 | 81.5B | 1,000 | 53.1A |
| 1,000 | 98.3A | | |

[1]Concentration of the active ingredient expressed as ppm.
[2]Inhibition of vegetative growth expressed as percent of the untreated control.
[3]Numbers followed by dissimilar letters, within columns, are significantly different (P = 0.05).

EXAMPLE 10

The efficiency of T. harzianum T-315 (ATCC 20671) in integrated control, using both a chemical fungicide and the T. harzianum T-315 (ATCC 20671) was investigated and compared with the efficacy of the chemical fungicide or the T. harzianum preparation alone.

Gypsophila cuttings were grown in peat, naturally infested with Pythium aphanidermatum and Rhizoctonia solani and were tested for disease percentage after various treatments.

*T. harzianum* alone was found to be efficient in controlling both *P. aphanidermatum* and *R. solani*. It was found to be competent, as well for integrated control since it provides a marked improvement when used together with the fungicide previcur. Integrated treatment reduced both Pythium and Rhizoctonia diseases, while application of previcur alone resulted in a reduction of Pythium incidence but an increase in Rhizoctonia incidence even beyond the level of the control. Results are shown below in Table 7.

TABLE 7

Effects of *T. harzianum* T-315 (ATCC 20671) and the Integration of Same with the Fungicide Previcur on *P. aphanidermatum* and *R. solani* Diseases in Gypsophila Cuttings.

| | Diseased Plants[1] | | |
|---|---|---|---|
| | Total Diseased Plants (%) | R.[2] Diseased Plants (%) | P.[2] Diseased Plants (%) |
| Control | 97.9A[4] | 44.3B | 53.6A |
| T. harzianum (T-315) | 61.8C | 37.2C | 24.6B |
| Previcur[3] | 80.5B | 62.9A | 17.6B |
| T. harzianum (T-315) + Previcur | 22.4D | 15.8D | 6.6C |

[1]The number of the diseased plants was determined two weeks after planting.
[2]R. - *Rhizoctonia solani*; P. - *Pythium aphanidermatum*.
[3]Previcur was applied at a rate of 1.5 ml/l water/m$^2$.
[4]Numbers followed by dissimilar letters within columns are significantly different (P = 0.05).

EXAMPLE 11

The effects of soil fumigation with methyl bromide prior to application of Trichoderma on development of *S. rolfsii* disease was studied on tomato plants. Tomato seedlings were grown in the nursery in pots containing peat, 15% of which comprised *T. harzianum* T-315 (ATCC 20671). The seedlings were transferred to the field and planted in plots, some of which had previously been fumigated with methyl bromide, and others of which had not.

Integrated control, i.e., fumigating with methyl bromide followed by application of *T. harzianum* was shown to be the preferable treatment. Application of the Trichoderma to the rhizosphere of the seedlings enabled massive development of the Trichoderma population, thus keeping the seedlings healthy and fruitful. The results are presented below in Table 8.

TABLE 8

The Effects of Soil Fumigation by Methyl Bromide and Trichoderma T-315, (ATCC 20671), Application in the Rhizosphere of Tomato Seedlings on the Control of *S. rolfsii* Disease and on Tomato Yield.

| Field Treatments | Application of Trichoderma | Trichoderma Propagules in Soil (no./g) | Diseased Plants (%) | Tomato Yield (kg/1000 m$^3$) |
|---|---|---|---|---|
| Control | — | | 22.0 C[1] | 451 A |
| | + | 2,250 | 12.0 B | 707 B |
| Methyl bromide fumigation | — | 1,520 | 7.0 B | 652 B |
| | + | 7,100 | 1.5 A | 1,177 C |

[1]Numbers followed by dissimilar letters within columns are significantly different (P = 0.05).

EXAMPLE 12

Cotton was planted in soil infested with Fusarium spp. *T. harizianum* T-315 (ATCC No. 20671) was incorporated into the soil as a composition comprising wheat bran:peat (1:1) v/v, at 5 grams of composition per kilogram of soil. The experiment was carried out in greenhouses. After thirty days the plants were inspected. The results are shown in Table 9 below.

TABLE 9

The effect of *T. harzianum* T-315, (ATCC 20671), on Fusarium spp.

| Treatment | Diseased Plants % | Disease Reduction % |
|---|---|---|
| Control | 41.3 | — |
| T-315 | 14.8 | 64.2 |

What is claimed is:

1. A biologically pure, stable culture of a strain of a mycoparasite of the species *Trichoderma harzianum* designated *Trichoderma harzianum* Rifai T-315 (ATCC No. 20671) or a mutant derived therefrom useful as a biological control agent.

2. A culture in accordance with claim 1 additionally having resistance to an amount of a chemical antagonist capable of substantially retarding the growth of or of killing other fungi.

3. A culture in accordance with claim 2, wherein the chemical antagonist is a pesticide.

4. A culture in accordance with claim 3, wherein the pesticide is a fungicide.

5. A culture in accordance with claim 4, wherein the fungicide is pentachloronitrobenzene; N-(trichloromethylthio)-4-cyclohexene-1, 2-dicarbonoximide; P-dimethylaminobenzenediazo sodium sulfonate or S-ethyl N-(3-dimethylaminopropyl) thiocarbamate.

6. A culture in accordance with claim 2, wherein the chemical antagonist is a soil-sterilant.

7. A culture in accordance with claim 6, wherein the soil-sterilant is methyl bromide.

8. A biocontrol composition comprising an effective amount of the culture of claim 1 and a suitable agronomically acceptable carrier.

9. A biocontrol composition in accordance with claim 8, wherein the concentration of the mycoparasite contained in the culture is at least 10$^5$ spores per gram of composition.

10. A biocontrol composition in accordance with claim 8 wherein the mycoparasite contained in the culture is present in the form of conidia or chlamydospores or mixtures thereof.

11. A biocontrol composition in accordance with claim 8 wherein the carrier includes a food base for the mycoparasite contained in the culture.

12. A biocontrol composition in accordance with claim 8 which also comprises a chemical pesticide.

13. A biocontrol composition in accordance with claim 12, wherein the chemical pesticide is a fungicide.

14. A biocontrol composition in accordance with claim 13, wherein the fungicide is pentachloronitrobenzene; N-(trichloromethylthio)-4-cyclohexene-1, 2-dicarboximide; P-dimethhylaminobenzendiazo sodium sulfonate or S-ethyl N-(3-demethylaminopropyl) thiocarbamate.

15. A biocontrol composition in accordance with claim 8, which also comprises a suitable agriculturally acceptable adhesive.

* * * * *

UNITED STATES PATENT AND TRADEMARK OFFICE
CERTIFICATE OF CORRECTION

PATENT NO. : 4,713,342
DATED : December 15, 1987
INVENTOR(S) : Ilan Chet, Alex Sivan and Yigal Elad It is certified that error appears in the above-identified patent and that said Letters Patent is hereby corrected as shown below:

Delete Col. 9, lines 35-66 (Example 11 and Table 8)

Column 10, line 2, "Example 12" should read

-- Example 11 -- ; line 9, "9" should read -- 8 --;

line 10, "9" should read --8 --.

Signed and Sealed this

Second Day of August, 1988

Attest:

DONALD J. QUIGG

Attesting Officer

Commissioner of Patents and Trademarks